(12) United States Patent
Yanai et al.

(10) Patent No.: US 7,727,961 B2
(45) Date of Patent: Jun. 1, 2010

(54) ANTIOXIDANT CONSTITUENTS

(75) Inventors: Nobuya Yanai, Tokyo (JP); Shigenobu Shiotani, Shizuoka (JP); Satoshi Kanazawa, Ibaraki (JP)

(73) Assignee: Tokai Bussan Co., Ltd., Tokyo (JP)

( * ) Notice: Subject to any disclaimer, the term of this patent is extended or adjusted under 35 U.S.C. 154(b) by 991 days.

(21) Appl. No.: 11/118,368

(22) Filed: May 2, 2005

(65) Prior Publication Data

US 2005/0250703 A1 Nov. 10, 2005

(30) Foreign Application Priority Data

Apr. 30, 2004 (JP) ............................. 2004-136934
Mar. 23, 2005 (JP) ............................. 2005-085028
Apr. 22, 2005 (JP) ............................. 2005-125601

(51) Int. Cl.
*A61K 38/05* (2006.01)
*A61K 38/04* (2006.01)

(52) U.S. Cl. .......................................... 514/18; 514/19

(58) Field of Classification Search ....................... None
See application file for complete search history.

(56) References Cited

U.S. PATENT DOCUMENTS 5,977,073 A * 11/1999 Khaled ......................... 514/19
6,048,846 A * 4/2000 Cochran ...................... 514/168
6,352,712 B1 * 3/2002 Lukaczer et al. ............. 424/439

FOREIGN PATENT DOCUMENTS

JP 2004-231902 8/2004

OTHER PUBLICATIONS

Wolfe and Liu. Apple peels as value added food ingredient. J Agric Food Chem 51:1676-1683, 2003.*
Candalish and Das. Antioxidants in Food and chronic degenerative diseases. Biomedical and Environmental Sciences 9:117-123, 1996.*
Slavin et al Whole grain consumption and chronic disease: protective mechanisms. Nutr Cancer 27:14-21, 1997.*
Sies and Stahl. Vitamins E and C, beta-carotene, and other carotenoids and antioxidants. Am J Clin Nutr 62:1315S-1321S, 1995.*
Kwong et al. Effects of Coenzyme Q10 Administration on its Tissue Concentrations, Mitochondrial Oxidant Generation, and Oxidative Stress in the Rat Free Radic Biol Med. 33:627-638; 2002.*
D'Agostini et al. Interactions between NAC and ascrobic acid in modulating mutagenesis and carciongensis. Int J Cancer 88:702-707, 2000.*

Bendich and Olson. Biological actions of carotenoids. FASEB J 3:1927-1932, 1989.*
Adang et al. Synthesis and nucleophilic reactivity of a series or glutatione analogues, modified at the gama-glutamyl moiety. Biochem J 255:715-720, 1988.*
Son and Lewis. Free radical scavenging and antioxidative activity of caffeic acid amide and ester analogues: structure-activity relationship. J Agric Food Chem 50, 468-472, 2000.*
Choi et al (Biochem et Biophysica Acta 1472:651-657, 1999).*
J. Kaikkonen et al., Antioxidative Efficacy of Parallel and Combined Supplementation with Coenzyme Q10 and d-α-Tocopherol in Mildly Hypercholesterolemic Subjects: a Randomized Placebo-Controlled Clinical Study., Free Radical Research, vol. 33, pp. 329-340 (2000).
Nobuya Yanai, et al., "Purification and Characterization of Antioxidative Dipeptides Anserine and Carnosine in Chicken Extract", Proceedings of the United States-Japan Cooperative Program in Natural Resources, Food and Agriculture Panel, pp. 125-128, Oct. 23-29, 2005.
Nobuya Yanai, et al. "Antioxidant Combination Inhibits Reactive Oxygen Species Mediated Damage", Biosc. Biotechnol, Biochem. 72(12), pp. 3100-3106, 2008.
Margreet R. Olthof, et al., Human Nutrition and Metabolism "Chlorogenic Acid and Caffeic Acid Are Absorbed in Humans", In The Journal of Nutrition, 131: pp. 66-71, 2001.
Richard S. Bruno, et al., "Human vitamin E requirements assessed with the use of apples fortified with deuterium-labeled α-tocopheryl acetate" The American Journal of Clinical Nutrition, 2006: 83: pp. 299-304.

* cited by examiner

*Primary Examiner*—Brandon J Fetterolf
*Assistant Examiner*—Craig Ricci
(74) *Attorney, Agent, or Firm*—Oblon, Spivak, McClelland, Maier & Neustadt, L.L.P

(57) ABSTRACT

An object of the present invention is to provide an antioxidant composition that is effective in the living body against active oxygen species produced in the body. The present invention provides an antioxidant composition having the effect of suppressing three active oxygen species, i.e. hypochlorite radicals, hydroxyl radicals, and peroxynitrite radicals, with respect to active oxygen species produced in the body, the antioxidant composition comprising a mixture in which at least 20 mg of vitamin C (L-ascorbic acid or sodium L-ascorbate) as an agent to scavenge peroxynitrite active oxygen, and at least 2 mg of caffeic acid analogue compound(s), at least 10 mg of polyphenyol compound(s) or at least 1.5 mg of carotenoid compound(s) as an agent to scavenge hydroxyl radical active oxygen are combined with 100 mg of histidine-containing dipeptide, or sulfur-containing amino acids or analogues thereof obtained from animal extract as an agent for scavenging hypochlorite active oxygen.

8 Claims, 11 Drawing Sheets

1 Control
2 ClO·-scavenger
3 OH·-scavenger
4 ONOO·-scavenger
5 Antioxidant mixture

ANTIOXIDANT CONSTITUENTS

BACKGROUND OF THE INVENTION

1. Field of the Invention

The present invention relates to a composition having antioxidative activity that is derived from natural extracts of animals and plants, and more particularly to an antioxidant composition that can exhibit anti-oxidative activity in the living body against active oxygen species which are produced in the body. The present invention provides a novel antioxidant composition that enables the preparation of food products and food product ingredients that provide protection against a wide range of lifestyle diseases, more specifically, protection against diabetes-related diseases in diabetic patients who have a markedly high level of active oxygen, by eliminating oxidative stress caused by active oxygen produced within the body.

2. Description of Related Art

In recent years in Japan the increasing number of various geriatric diseases associated with an aging population and the increased human and economic burden of medical care thereof have become extremely serious problems. The aging of organisms and the onset of disease are, in a sense, inextricably related, and therefore it is unavoidable that as the population ages, the number of people with diseases will also increase. Thus, it is important to delay the progression of aging in humans as much as possible to suppress the onset of disease.

The primary cause of aging in human beings is the fact that the cells constituting the body are limited in the number of times they can divide and propagate to regenerate tissue, and the number of cellular divisions reaches its limit and tissue regeneration capability decreases because cells are subjected to various kinds of damage. Aging progresses due to factors that damage cells, for example, exposure to ultraviolet light and radiation, chemicals, etc., and to active oxygen that is produced within the bodies of living organisms. More specifically, active oxygen is a substance that is naturally produced by organisms that utilize oxygen to perform energy metabolism, and in that sense, it can be said that the aging we undergo occurs naturally. Therefore, the suppression of the harmful effects of active oxygen that is produced within the body plays an important role as a primary countermeasure to delay aging and suppress the onset of age-related diseases.

In the past various antioxidants have appeared on the market, but almost all were prepared from a single constituent or single starting material. However, there are many different active oxygen species produced in the body, and concrete examples include superoxide ($O_2^-$) produced from oxygen gas incorporated into the body. This $O_2^-$ is converted to hydrogen peroxide ($H_2O_2$) by an enzyme called superoxide dismutase (SOD), and the $H_2O_2$ goes on to generate a hydroxyl radical (OH•) by transition metal catalysis. In addition to $H_2O_2$, white blood cells produce active oxygen to destroy bacteria that invade the body, and these forms of active oxygen include the hypochlorite radical, nitric oxide radical, etc.

On the one hand, various species of antioxidants are used to remove these types of active oxygen, but sufficient investigations have not been performed to determine whether these antioxidants are effective against all active oxygen species or only a limited number of species thereof. The inventors investigated the effects of antioxidants on the oxidative degradation of protein by various active oxygen species, and these investigations revealed that different antioxidants are effective against different active oxygen species, and there are very few antioxidants that are effective against all active oxygen species in the body. In other words, substances that have potent antioxidative action include the following: against the hypochlorite radical (ClO•), the peptides anserine and carnosine, reduced glutathione (GSH), and sulfur-containing amino acids or analogs thereof that are present in the bodies of various species of animals; against the peroxynitrite radical (ONOO•), vitamin C (L-ascorbic acid, V.C.); and against the hydroxyl radical (OH•), vitamin E (α-tocopherol, V.E.). It has already been confirmed that combinations and compositions of antioxidants wherein antioxidants are used together rather than independently are effective in completely eliminating the damage caused by active oxygen produced in the body (see Japanese Patent Application No. 2003-025210).

In the past various antioxidants have been tested for the prevention of various types of diseases, and lifestyle diseases in particular. For example, these include polyphenols such as V.C., V.E., β-carotene, catechins, etc. However, when we look at the prevention of diseases, e.g., the prevention of diseases such as cancer, etc., by these antioxidants, few findings show that they are effective. Conversely, most results show that they have no clinical efficacy (see J. Kaikkonen, et al. Free Radicals Research, Vol. 33, p. 329-340, 2000), and antioxidants have not provided the effect of preventing diseases and aging as much as had been expected. Possible causes include the following: first, there are many active oxygen species produced in the body, and it is almost impossible to eliminate all of their damaging effects with a single antioxidant; furthermore, with the exception of V.C., most of the other antioxidants derived from plants have a structural backbone such as a phenol group, etc., that exhibits the property of lipid solubility, and polyphenols are so poorly absorbed by the human gastrointestinal tract that the amount absorbed into the body is no more than $\frac{1}{1000}$ of the amount ingested orally, etc. Therefore, most of these antioxidants have not sufficiently displayed efficacy in the body even when they have demonstrated extremely potent antioxidant activity in vitro.

To overcome these deficiencies, it is important to have an antioxidant composition that can counteract the wide range of active oxygen species and to select materials that can sufficiently counteract the OH• produced in the process of energy metabolism. As noted above, the peptides anserine and carnosine, reduced glutathione (GSH), and sulfur-containing amino acids obtained from animal materials have strong antioxidant activity against ClO•; V.C., which is a water-soluble vitamin, has strong antioxidant activity against ONOO•; and V.E., which is a fat-soluble vitamin, has strong antioxidant activity against OH•. However, the strong antioxidant activity of V.E. against OH• is one that inhibits proteolysis, and when we compare it with other antioxidants derived from plants, this activity is approximately $\frac{1}{5000}$ that of the carotenoid astaxanthin, $\frac{1}{2000}$ to $\frac{1}{1000}$ that of the polyphenol catechins and quercetin, and $\frac{1}{1000}$ to $\frac{1}{500}$ that of caffeic acid derivatives (Table 1). Therefore, even though V.E. is absorbed well by the gastrointestinal tract and it is distributed throughout the whole body, a large amount must be ingested to scavenge OH•. However, there are problems with V.E. because the maximum daily dose to be taken by adults is 300 mg, it is harmful if taken in excess, and because it is an oil, it suffers a loss of antioxidant activity during storage and food processing becomes difficult.

SUMMARY OF THE INVENTION

After reviewing the above prior art and reflecting on the status quo, the inventors conducted diligent research with the goal of developing a novel antioxidant composition that will enable solution of the aforementioned problems, and upon searching for antioxidant ingredients having strong OH•-scavenging capability to replace or potentiate V.E., they discovered that, as noted above, polyphenols such as catechins and quercetin, phenol compounds such as the caffeic acid analogues curcumin and ferulic acid, and the carotenoids astaxanthin and β-carotene have potent antioxidative action against OH•(FIG. 1). The inventors also discovered that because these antioxidants with potent OH•-scavenging activity have, similarly to V.E., the property of exhibiting almost no antioxidative activity against ClO• and ONOO• at physiologically relevant low concentrations, it is essential that they used in combination with the ClO•-scavenging anserine-carnosine mixture and the ONOO•-scavenger V.C., thus arriving at the present invention.

An object of the present invention is to provide an antioxidant composition that exhibits antioxidative capability in the body against a variety of active oxygen species produced in the body.

To solve the above problems, the present invention consists of the following technical means.

(1) An antioxidant composition having the effect of suppressing three active oxygen species, i.e. hypochlorite radicals, hydroxyl radicals, and peroxynitrite radicals, with respect to active oxygen species produced in the body, the antioxidant composition comprising a mixture in which at least 20 mg of vitamin C (L-ascorbic acid or L-ascorbate) as an agent to scavenge peroxynitrite active oxygen, and at least 2 mg of caffeic acid analogue compound(s), at least 10 mg of polyphenyol compound(s) or at least 1.5 mg of carotenoid compound(s) as an agent to scavenge hydroxyl radical active oxygen are combined with 100 mg of histidine-containing dipeptide, or sulfur-containing amino acids or analogues thereof as an agent for scavenging hypochlorite active oxygen.

(2) The antioxidant composition according to (1) above, wherein the histidine-containing dipeptide of the agent for scavenging hypochlorite active oxygen is a mixture of anserine and carnosine, which are histidine-containing peptides contained in animal extract that is obtained by extraction with hot water from the muscles of poultry, cattle, pigs, and migratory fish, and the sulfur-containing amino acid or analogue thereof is one or more species of reduced glutathione, cysteine, acetylcysteine, methionine, and alliin obtained from extracts of plants of the Allium or Brassica families.

(3) The antioxidant composition according to (1) above, wherein the caffeic acid analogue is one extracted from plants of the wheat or poaceae families.

(4) The antioxidant composition according to (1) above, wherein the polyphenol compound is the catechin extracted from mulberry leaves or tea leaves, and/or the quercetin extracted from the Allium family.

(5) The antioxidant composition according to (1) above, wherein the carotenoid compound is astaxanthin extracted from fish meat or algae, and/or the β-carotene extracted from plants selected from ashitaba (*Angelica keiskei*), pumpkin, carrot, mugwort, perilla, or kale.

(6) The antioxidant composition according to (1) above which has an effect of lowering concentration of water-soluble cholesterol in blood, wherein at least 20 mg of vitamin C (L-ascorbic acid or L-ascorbate) as an agent to scavenge peroxynitrite active oxygen, and at least 2 mg of caffeic acid analogue compound(s) as an agent to scavenge hydroxyl radical active oxygen are combined with 100 mg of the histidine-containing dipeptide, or sulfur-containing amino acids or analogues thereof as an agent for scavenging hypochlorite active oxygen.

(7) The antioxidant composition according to (1) above, wherein histidine-containing dipeptide, or sulfur-containing amino acids or analogues thereof as an agent for scavenging hypochlorite active oxygen is a mixture of anserine and carnosine, and the caffeic acid anclogue compound(s) a water soluble ferulic acid, chlorogenic acid, cinnamic acid, or caffeic acid.

(8) The antioxidant composition according to (1) above, wherein at least 20 mg of vitamin C (L-ascorbic acid or L-ascorbate) as an agent to scavenge peroxynitrite active oxygen, and at least 2 mg of ubiquinone compound as an agent to scavenge hydroxyl radical active oxygen are combined with 100 mg of the histidine-containing dipeptide, or sulfur-containing amino acids or analogues thereof as an agent for scavenging hypochlorite active oxygen.

(9) The antioxidant food characterized by comprising the antioxidant composition defined in (1) above.

(10) The antioxidant food characterized by comprising the antioxidant composition defined in (6) above.

(11) The antioxidant food characterized by comprising the antioxidant composition defined in (8) above.

Next, the present invention will be further described in detail.

The effective use of antioxidants derived from animal extracts complements the deficiencies of antioxidants derived from plant extracts and vice versa; therefore, natural materials containing the aforementioned ClO•-scavenger, OH•-scavenger and ONOO•-scavenger were selected to constitute an antioxidant composition that can completely scavenge three active oxygen species produced in the body. The anserine-carnosine mixture having a potent ClO•-scavenging action is contained in abundance in the extracts of various meat, chicken, and the meat of large migratory fish such as tuna, bonito, salmon, etc.; sulfur-containing amino acids are contained in abundance in the extracts of Allium plants such as onions and Brassica plants such as cabbage. V.C. having a potent ONOO•-scavenging action is contained in large amounts in citrus fruits and in the extracts of Brassica plants such as cabbage, etc. On the other hand, with respect to the carotenoids such as astaxanthin and β-carotene having potent OH•-scavenging action, the former is contained in abundance in the extract of salmon, which is an animal, and extracts of algae, whereas the latter is contained in abundance in the extracts of green and yellow vegetables such as carrots, etc.; polyphenols such as catechins, epigallocatechin gallate, quercetin, etc., are contained in the respective extracts of plants such as mulberry leaves, green tea, onions, etc. In addition, among the caffeic acid analogues having a potent OH•-scavenging action, curcumin is contained in abundance in the extract of tumeric, and ferulic acid, etc., are contained in abundance in extracts obtained from wheat and rice, for example, wheat grass extract and rice bran extract, etc. In practice, when the OH•-scavenging capability of these extracts was tested, each demonstrated a potent antioxidant action toward OH• (FIG. 2).

With respect to the doses or amounts of these antioxidants to be ingested by humans, there are no established doses; for example, the recommended daily amount for V.C. ranges from ≧60 mg to ≦200 mg, and for V.E. from ≧3 mg to ≦300 mg. Based on these amounts, when the dose or amount to be ingested of each type of ingredient was estimated from the results of tests conducted in the present invention, the following were obtained.

At a concentration of 5 mM, anserine-carnosine, anserine-carnosine mixture or sulfur-containing amino acids, which are agents that scavenge ClO•, had sufficient antioxidant action to completely inhibit the proteolytic action of a 10 mM concentration of ClO•. On the other hand, a 1 mM concentration of V.C. or sodium V.C. completely inhibited the oxidative effect of a 5 mM concentration of ONOO•. Furthermore, a 0.5 µM concentration of carotenoids, 2.5 µM concentration of caffeic acid, or 2.5 µM concentration of polyphenols completely inhibited the oxidative action of a 10 mM concentration of OH•. There is a problem with the gastrointestinal absorption of polyphenols, and because among the active oxygen species produced in the body, OH• is produced in large quantities, the amount of polyphenols in the composition needs to be set higher.

The concentration of active oxygen produced in the body changes depending on the physiological conditions, but it is estimated to reach maximum levels of several 10 µM to several 100 µM locally, and if we standardize the minimum blood concentration of each antioxidant when the antioxidant composition of the present invention is taken once a day, an amount equivalent to 500 µM of the ClO•-scavenger anserine-carnosine (a dose of approximately 600 mg calculated for a blood volume of 5000 mL), an amount equivalent to 200 µM of the ONOO•-scavenger V.C. (a dose of approximately 90 mg), and in consideration of the proportion of OH• produced in the body, for the OH•-scavengers, amounts equivalent to 0.5 mM of carotenoids (a dose of approximately 1.5 mg), 2.5 µM of caffeic acid analogue (a dose of 5 to 10 mg), and 2.5 mM of polyphenols (a dose of 4 mg) should be sufficient to prevent the damaging effects of active oxygen. If the amount of each ingredient is expressed per 100 mg of the ClO•-scavenger anserine-carnosine mixture or sulfur-containing amino acids such as reduced glutathione, etc., the calculated amounts in the composition are 20 mg or more of the ONOO•-scavenger V.C., and in consideration of the gastrointestinal absorption of the OH•-scavengers, 1.5 mg or more of carotenoids for a minimum blood concentration (M. Osterile, et al., Journal of Nutritional Bichemistry, No. 11, p. 482-490, 2000), 2 mg or more of caffeic acid analogues, which encounter no particular problem with gastrointestinal absorption, and 1 mg or more of polyphenols such as catechins; however, in consideration of gastrointestinal absorption, a 10-fold greater amount of 10 mg or more is preferred (F. Catterall et al., Xenobiotica, No. 33, p. 743-753, 2003).

The antioxidants of the present invention wherein these OH•-scavengers are modified are ones that have antioxidant activity equivalent to a composition containing 20 mg of V.C. and 20 mg of V.E. per 100 mg of anserine-carnosine mixture, and it has been found that the formulation of combinations of a food ingredients with a an extremely wide range of selection branches from animal extracts to various plant extracts is possible, and the formulation of antioxidant foods that can prevent the harmful effects of active oxygen produced in the body becomes easier thereby.

In the present invention, the each ingredient can be arranged in the form of the chemical compound itself or the material containing the compound derived from natural sources. The present invention is characterized in that the antioxidant agent, food or food material containing the antioxidant compound or material as the main ingredient which is constructed as the specific subject matter of the present invention has the effect of scavenging 3 types of the active oxygens of ClO• redical, OH• radical and NO3• radical simultaneously in the body, said radicals are produced in the body. The above specific subject matter and the effect thereof are not obvious from the general knowledge in the field of the art to which the present invention is belonged.

Next, the test examples of the present invention are described even more concretely.

(1) Inhibitive Effects of Various Antioxidants on Ovalbumin (hereinafter, Ova) Degradation by Three Active Oxygen Species ClO•, OH•, and $NO_3$• were prepared as three typical active oxygen species produced in the body. Clo• was prepared using a method wherein sodium hypochlorite was diluted to a pH 6.5 with distilled water, OH• by a partially modified Fenton method (B. Halliwell, et al., Analytical Biochmistry, No. 165, p. 215-219, 1987), and NO3• by a modified quenching flow reactor method (R. Radi, et al., Journal of Biological Chemistry, Vol. 266, p. 4244-4250, 1991). Next, Ova was dissolved in pH 7.2 buffered physiological saline to a concentration of 2.5 mg/mL, each concentration of antioxidant was added at a volume ratio of 10:1 with respect to the protein solution, the solution was let stand for 30 min at room temperature, each concentration of active oxygen was added in the same manner at a volume ratio of 10:1 with respect to protein solution, and ClO• oxidation was performed for 30 min at 37° C., OH• oxidation for 60 min at 37° C., and $NO_3$ oxidation for 120 min at 37° C. After the reaction, sodium dodecylsulfate-polyacrylamide gel electrophoresis (SDS-PAGE) was performed on each sample, the gel was stained with Coomassie blue R250, and the Ova degradation inhibition rate was calculated from the densitometer reading. An accurate degradation inhibition rate was calculated using the following formula from the proteolytic inhibition activity obtained by performing GPC-HPLC using a TSKG-3,000SW column directly on the reacted samples.

Degradation rate(%)=(Peak area of protein degraded by active oxygen at the time the antioxidant was added/Peak area of undegraded control protein)×100

FIG. 1 shows the inhibitory action of each antioxidant toward Ova oxidative degradation by the three active oxygen species. With respect to ClO•, the purified anserine-carnosine mixture from chicken extract completely inhibited oxidative degradation by ClO•; in addition, faint inhibitory activity was seen with by V.C., β-carotene and epigallocatechin gallate (EGCG). The concentrations of β-carotene and EGCG were 20 µM and 500 µM, respectively, but these are concentrations equivalent to no less than 100 times concentrations that are physiologically relevant, so they were impractical. With respect to OH•, 10 µM of astaxanthin and β-carotene, and 5 µM of catechins, quercetin, ECGC, and the caffeic acid analogues curcumin, chlorogenic acid, and ferulic acid completely inhibited the oxidative degradation of Ova, at the same level as V.E. with a concentration of 5 mM did. With respect to ONOO•, 1 mM of V.C. completely inhibited the oxidative degradation, and in addition, β-carotene, catechins, and EGCG showed degradation inhibitory activity at respective concentrations of 10 µM, 500 µM and 500 µM, but those concentrations exceed physiologically relevant concentrations. Table 1 summarizes the degradation inhibitory activity.

TABLE 1

Inhibitory Action of Antioxidants toward Proteolysis by Various Active oxygen species (%)

| Antioxidant | ClO radical | OH radical | ONOO radical |
|---|---|---|---|
| Anserine-carnosine (5 mM) | 100 | 0 | 14 |
| Vitamin C (5 mM) | 67 | 0 | 100 |
| Vitamin E (5 mM) | 0 | 98 | 22 |
| Astaxanthin (20 µM) | 24 | 100 | 28 |
| B-carotene (20 µM) | 38 | 100 | 74 |
| Catechins (50 µM) | 0 | 100 | 58 |
| Quercetin (50 µM) | 5 | 100 | 16 |
| Curcumin (500 µM) | 16 | 100 | 13 |
| Chlorogenic acid (50 µM) | 0 | 100 | 28 |
| Ferulic acid (50 µM) | 7 | 100 | 34 |

(2) Comparison of Effects of Antioxidant-Containing Natural Extracts on Three Species of Antioxidants Using the same test methods as described in (1) above, a comparison of inhibitory activity by various natural extracts on the Ova degradation by active oxygen was performed. The concentrations of the natural extracts tested were 5 mg/mL as solids. FIG. 2 shows the results of SDS-PAGE.

There were three types of natural extracts showing inhibitory effects on oxidative degradation by ClO•: chicken extract, salmon extract, and cabbage extract. Chicken extract contains anserine and carnosine, salmon extract contains anserine, and cabbage extract contains sulfur-containing amino acids and V.C. Salmon extract, carrot extract, green tea extract, tumeric extract, and cabbage extract exhibited strong inhibitory effects on oxidative degradation by OH•, and this was followed in order by inhibitory effects exhibited by wheat grass extract, rice bran extract, onion extract and mulberry leaf extract. The inhibitory effects of chicken extract and lemon juice were extremely weak. Salmon extract contains not only anserine, but also astaxanthin, carrot juice contains β-carotene, green tea extract contains EGCG, tumeric extract contains curcumin, and cabbage extract contains not only sulfur-containing amino acids and V.C., but also catechins and caffeic acid analogues. Wheat grass extract and rice bran extract contain caffeic acid analogues such as ferulic acid, etc., onion extract contains quercetin, and mulberry leaf extract contains catechins and caffeic acid analogues. Lemon extract exhibited the most potent inhibitory effect on oxidative degradation by ONOO•, and inhibitory effects on oxidative degradation were also seen with salmon extract, onion extract, cabbage extract, and chicken extract. With respect to the main ingredients of these extracts, lemon juice and cabbage contain V.C., Onions and mulberry leaves contain not only V.C. but also reduced glutathione and catechins, and chicken extract and salmon extract contain not only anserine and carnosine, but also various amino acids. Table 2 shows a summary of these antioxidant effects.

TABLE 2

Effects of Various Natural Extracts on Proteolysis by Each Active Oxygen Species

| Natural extract (solids 0.5%) | ClO radical | OH radical | ONOO radical |
|---|---|---|---|
| Chicken extract | 100 | 28 | 82 |
| Lemon juice | 52 | 12 | 100 |
| Rice bran extract | 0 | 100 | 12 |
| Salmon extract | 100 | 100 | 100 |
| Carrot extract | 4 | 100 | 28 |
| Mulberry leaf extract | 12 | 76 | 52 |
| Onion extract | 38 | 92 | 88 |
| Green tea extract | 0 | 100 | 40 |
| Tumeric extract | 0 | 100 | 0 |
| Cabbage extract | 89 | 100 | 73 |
| Wheat grass extract | 16 | 98 | 52 |

(3) Comparison of Active Oxygen Removal Effect by Each Antioxidant

The strength of antioxidant activity between peptides with antioxidant activity and sulfur-containing amino acids was compared with respect to ClO•, and between various antioxidants with antioxidant activity with respect to OH•. Table 3 shows a comparison of the concentrations of various antioxidants with ClO•-scavenging action that completely inhibit the oxidative degradation of proteins shown by a concentration of 10 mM of ClO•; reduced glutathione, L-cysteine, and N-acetyl-L-cysteine were the most potent, followed in order by anserine and carnosine dipeptides, methionine, cysteic acid and alliin.

TABLE 3

Strength of ClO.- Scavenging Action

| Antioxidant | ClO radical inhibitory concentration (mM) |
|---|---|
| Anserine | 5.0 |
| Carnosine | 5.0 |
| Anserine-carnosine mixture | 5.0 |
| Reduced glutathione | 2.5 |
| Cysteine | 2.5 |
| N-acetyl-L-cysteine | 2.5 |
| Cysteic acid | 7.5 |
| Methionine | 5.0 |
| Alliin | 7.5 |

Table 4 shows the results of the comparison of the concentrations of various antioxidants that will completely inhibit the proteolytic action of a 10 mM concentration of OH• that was performed in the same manner for antioxidants with an antioxidant action on OH•. The strongest antioxidant effect against oxidative degradation of protein by OH• was shown by the carotenoids astaxanthin and β-carotene, the polyphenols quercetin and catechins, and the caffeic acid analogues curcumin, ferulic acid, chlorogenic acid, and caffeic acid in that order, and among the items tested V.E. had the weakest antioxidant activity.

TABLE 4

Strength of OH.-Scavenging Action

| Antioxidant | OH radical inhibitory concentration (µM) |
|---|---|
| Astaxanthin | 0.5 |
| B-carotene | 0.5 |
| Quercetin | 2.5 |
| Catechins | 2.5 |
| Epigallocatechin gallate | 2.5 |
| Curcumin | 2.5 |

TABLE 4-continued

Strength of OH.-Scavenging Action

| Antioxidant | OH radical inhibitory concentration (μM) |
| --- | --- |
| Ferulic acid | 2.5 |
| Chlorogenic acid | 3.0 |
| Caffeic acid | 4.0 |
| Vitamin E | 2500 |

(4) Effectiveness of Antioxidants in Preventing Damage by Active Oxygen on the Microchannel Transit Capability of Human Red Blood Cells A microchannel (hereinafter, MC), which is a capillary model, is a device that measures hemorheology, i.e., the capability of blood to circulate through capillaries. Factors affecting hemorheology include meals, oxidative stress, etc. In the present invention the effects of the three active oxygen species produced in the body on the MC transit capability of human red blood cells were tested, and the effectiveness of various antioxidants in preventing the harmful effects of active oxygen were compared.

For the test method, blood from healthy human volunteers was separated by a Ficoll-Paque centrifuge (made by Amersham-Pharmacia Biotech) into plasma, white blood cell, and a red blood cell fractions, and the MC transit time of each blood fraction was measured by an MC FAN KH-3A (channel width 7 μm, MC Laboratory, Inc.) The results show that transit damage due to the three active oxygen species, ClO•, OH•, and ONOO•, appeared in white blood cells (No. of nucleated cells: $2 \times 10^5$ cells/mL) and red blood cells (hematocrit 15%), but the transit capability of plasma (diluted 1:1) was unaffected (FIG. 3). Next, the effectiveness of various antioxidants in preventing the MC transit damage due to various active oxygen species was measured using red blood cells. FIG. 4 shows one example, and in this test an anserine-carnosine mixture (2.5 mM) from chicken extract as the ClO•-scavenger, EGCG (50 μM) as the OH•-scavenger, and V.C. (2.5 mM) as the ONOO•-scavenger were used. These three types were mixed together and used as the antioxidant mixture. As shown in FIG. 4, the red blood cell transit damage due to each species of antioxidant was completely inhibited by the respective antioxidants, and the antioxidant mixture was effective in completely inhibiting the damage caused by each active oxygen species.

(5) Effect of Lowering the Level of Glycated Hemoglobin in the Blood of Diabetic Model Rats Using the diabetes model animal GK rats (Y. Ihara, et al. FEBS Letters, Vol. 473, p. 24-26, 2000), the effectiveness of single doses of various antioxidants and combined doses of antioxidants in lowering the level of glycated hemoglobin (HbAlc) in the blood was compared. It is known that there is a strong correlation between the mortality rate of patients with cardiovascular disease occurring concurrently with diabetes and the level of HbAlc in the blood; with a decrease of 0.1% in the HbAlc concentration, a drop of 5% in the mortality rate can be expected, and with a decrease of 0.2%, a drop of 10% can be expected (K. T. Khaw, et al. BMJ, Vol. 322, p. 1-6, 2001).

As the ClO•-scavenger 200 mg/kg of anserine-carnosine mixture derived from chicken extract, as the OH•-scavenger wheat grass extract (total content of caffeic acid analogues 10 mg/kg), as the ONOO•-scavenger 100 mg/kg of V.C., and a composition containing all three antioxidants were administered orally to the GK rats for 28 days, and the blood HbAlc levels were measured at the end of dosing. As shown in FIG. 5, a decrease of 0.3% was seen with the ClO•-scavenger alone, a decrease of 0.2% was seen with the OH•-scavenger alone, a decrease of 0.3% was seen with the ONOO•-scavenger alone, and a decrease of 0.4% was seen with the composition that combined all three of the antioxidants; thus, the combination of the three species of antioxidants produced the best result in lowering the blood HbAlc concentration formed by the action of hyperglycemia and active oxygen.

(6) Effect of Lowering the Level of Cholesterol in the Blood of Human Body

It is known that, in the groups of the ingredients which have an antioxidant activity, there exist ingredients having some effect of lowering the level of cholesterol in the blood and that the functional mechanisms of the effect are various. As the mechanisms, for example, it seems that there exist the mechanism wherein the production of the energy from fat is facilitated to spend cholesterol in the body, the mechanism wherein the absorption of cholesterol via gut in the body is interrupted, the mechanism wherein the enzyme of synthesizing cholesterol is inhibited, and the mechanism wherein the ability to remove cholesterol by macrophage is accelerated and the like.

It is known that the chlorogenic acid and ferulic acid which are caffeic acid analogue compounds used in the present invention also have an effect of lowering the level of cholesterol in the blood as an agent for scavenging OH. Radical (A. Herrera-Arellano et al., Phytomedicine, Vol. 11, p. 561-566, 2004; H. K. Kim et al., Clinica Chimica Acta, Vol. 327, p. 129-137, 2003).

However, the effect of lowering the level of cholesterol in the body by the ferulic acid or chlorogenic acid which is ingested via oral administration is not elucidated and therefore, the inventors investigated whether the antioxidant component dosed via oral administration in the body has an effect of lowering the level of cholesterol in the blood.

The antioxidant food drink prepared by the method of Example 5, that is, 50 mL of mango juice which contains 400 mg of the purified anserine-carnosine mixture derived from chicken extract as the ClO•-scavenger, 20 mg of the ferulic acid derived from rice bran as the OH•-scavenger, and 300 mg of vitamin C as ONOO•-scavenger was administered via oral to 17 male members of healthy volunteers for 4 days by 1 piece/day to measure the amount of lipids in the blood sample thereof collected before and after the administration.

HDL cholesterol and neutral fat are measured as the lipids, and amount of LDL cholesterol was calculated according to the next formula, that is, the formula of LDL cholesterol=total cholesterol (HDL+neutral fat×0.2).

The results obtained is shown in FIG. 4-FIG. 6. With regard the value of the concentration of the total cholesterol in the blood of 12 members before the administration, the value was higher than 200 mg/dL before the administration, and the mean total cholesterol in the blood was lowered from 233.8±19.9 mg/dL to 219.3±24.2 mg/dL (p<0.05) after the administration. With regard to the value of LDL cholesterol of other 12 members before and after the administration, the value was higher than 120 mg/dL before the administration, and the mean LDL value in the blood was lowered from 149.0±16 mg/dL to 135.0±16.4 mg/dL (p<0.05) after the administration. With regard to the neutral fat, the value of cholesterol in the blood of 8 patients with high cholesterol value in the blood, the value was higher than 220 mg/dL before the administration, and the value thereof was lowered from 124.9±57.1 mg/dL to 91.6±29.4 mg/dL (p<0.05) after the administration.

(7) Effect of Agent Arranged with Three Ingredients

1) Inhibition Effects of Various Antioxidants on Ova Degradation by Three Active Oxygen Species The inhibitory action of each antioxidant toward Ova oxidative degradation by the three active oxygen species and agent arranged with three ingredients containing CoQ10 is shown in FIG. 9.

With respect to ClO radical (ClO•), the most strong inhibitory activity was seen with by the purified anserine-carnosine mixture from chicken extract, sulfur-containing amino acids and peptides, next, strong inhibitory activity was seen with by V.C., and CoQ10, however, did not inhibit the oxidative degradation of Ova. With respect to OH radical (OH•), 50 μM CoQ10 inhibited strongly the oxidative degradation of Ova and the inhibitory activity was not seen with by anserine-carnosine and vitamin C.

With respect to ONOO radical (ONOO•), V.C. completely inhibited the oxidative degradation of Ova, and faint inhibitory activity was seen with by the anserine-carnosine mixture from chicken extract, sulfur-containing amino acids-peptides and CoQ10. Antioxidant agent arranged with three ingredients of 5 mM anserin-carnosine mixture derived from chicken extract, 50 μM CoQ10 and 5 mM V.C. almost completely inhibited the oxidative degradation of Ova by three types of the active oxygen species, as shown in FIG. 9. The inhibition effects of various antioxidants on the degradation of protein due to each active oxygen are summarized in Table 5 as "Inhibition Effects of Various Antioxidants on the Degradation of Protein due to each Active Oxygen".

TABLE 5

Inhibition Effects of Various Antioxidants on the Degradation of Protein due to each Active Oxygen

| Antioxidant | ClO radical | OH radical | ONOO radical |
| --- | --- | --- | --- |
| Anserine-carnosine (5 mM) | 100 | 0 | 14 |
| Reduced glutathione (5 mM) | 100 | 18 | 29 |
| Cysteine (5 mM) | 100 | 15 | 22 |
| N-acetyl-L-cysteine (5 mM) | 100 | 20 | 20 |
| Methionine (5 mM) | 100 | 62 | 45 |
| Vitamin C (5 mM) | 67 | 18 | 100 |
| CoQ10 (50 μM) | 0 | 100 | 0 |
| Antioxidant composition with 3 ingredients* | 100 | 100 | 100 |

*Anserine-carnosine mixture from chicken extract (5 mM), CoQ10 (50 μM) and V.C. (5 mM)

2) Effectiveness of Antioxidants in Preventing Damage by Active Oxygen on the Microchannel Transit Capability of Human Red Blood Cells A microchannel (MC), which is a capillary model, is a device that measures hemorheology, i.e., the capability of blood to circulate through capillaries. Factors effecting hemorheology include meals, oxidative stress, etc. In the present Example, the effects of the three active oxygen species produced in the body on the MC transit capability of human red blood cells were tested.

For the test method, blood from healthy human volunteers was subjected a Ficoll-Pague centrifuge (made by Amersham-Pharmacia Biotech) to separate a red blood cell fraction, and the MC transit time of the red blood (final concentration of hematocrit is 10%) treated by various active oxygen species was measured by an MC FAN KH-3A (channel width 7 μm, MC Laboratory, Inc.). The results show that transit damage due to the three active oxygen species, ClO•, OH•, and ONOO• appeared in the red blood cells.

With respect to ClO•, anserine-carnosine mixture from chicken extract inhibited the MC transit damage, with respect to OH•, CoQ10 inhibited the damage, and with respect to ONOO•, V.C. inhibited the damage. In the case of antioxidative agent with 3 ingredients, the MC transit damage due to various radicals was completely inhibited (FIG. 10).

3) Effects of Improving Hemorheology in the Blood from Healthy Human Volunteers

To the healthy male volunteers (58 years old, 35 years old and 29 years old), 50 mL of juice drink containing 400 mg of anserine-carnosine mixture from chicken extract, 300 mg of vitamin C and 20 mg of CoQ10 was administracted via oral for 10 days by one piece/day to measure the effect of improving the liquidity of the blood samples of the volunteers before and after the administration by measuring the MC transit time by using the above MC FAN KH-3A. As the results, the mean MC transit time before the administration was 55.1 seconds, and the mean MC transit time after the administration was improved to 46.6 seconds (FIG. 11).

The present invention provides the following advantages:

(1) It divides the active oxygen species produced in the body into three groups and provides antioxidants that act effectively on each group;

(2) It identifies and formulates antioxidants against the OH• system produced from oxygen gas, and the chlorine system and nitric oxide system produced from white blood cells; and (3) It enables the provision of antioxidant food products that are effective in suppressing the onset of diseases associated with aging and lifestyle.

DETAILED DESCRIPTION OF THE INVENTION

Figure 1:
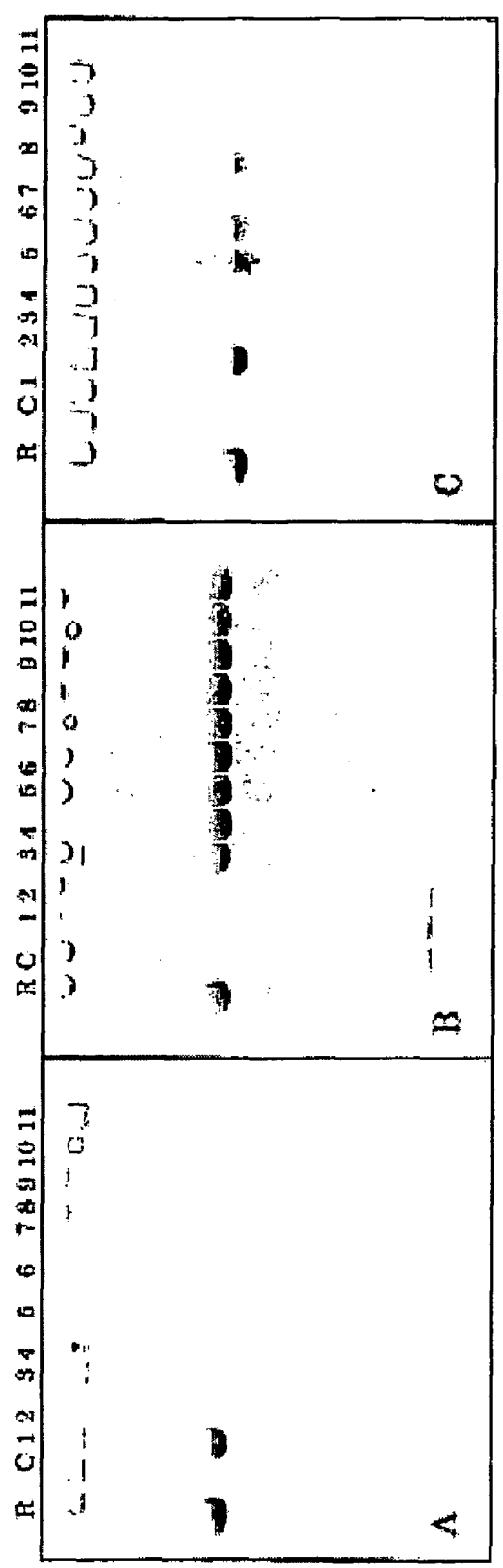
FIG. 1 shows the inhibitory effect of various antioxidants on ovalbumin degradation by active oxygen. A represents oxygen degradation by 10 mM of the ClO radical, B represents oxygen degradation by 10 mM of the OH radical, and C represents oxygen degradation by the ONOO radical. The symbols used in each panel for the added sample materials are as follows: R is untreated ovalbumin, C is oxidatively degraded control ovalbumin, 1 is the purified anserine-carnosine mixture, 2 is vitamin C, 3 is vitamin E, 4 is astaxanthin, 5 is β-carotene, 6 is catechin, 7 is quercetin, 8 is epigallocatechin gallate (EGCG), 9 is curcumin, 10 is chlorogenic acid, and 11 is ferulic acid (the concentrations are shown in Table 1)
Figure 2:
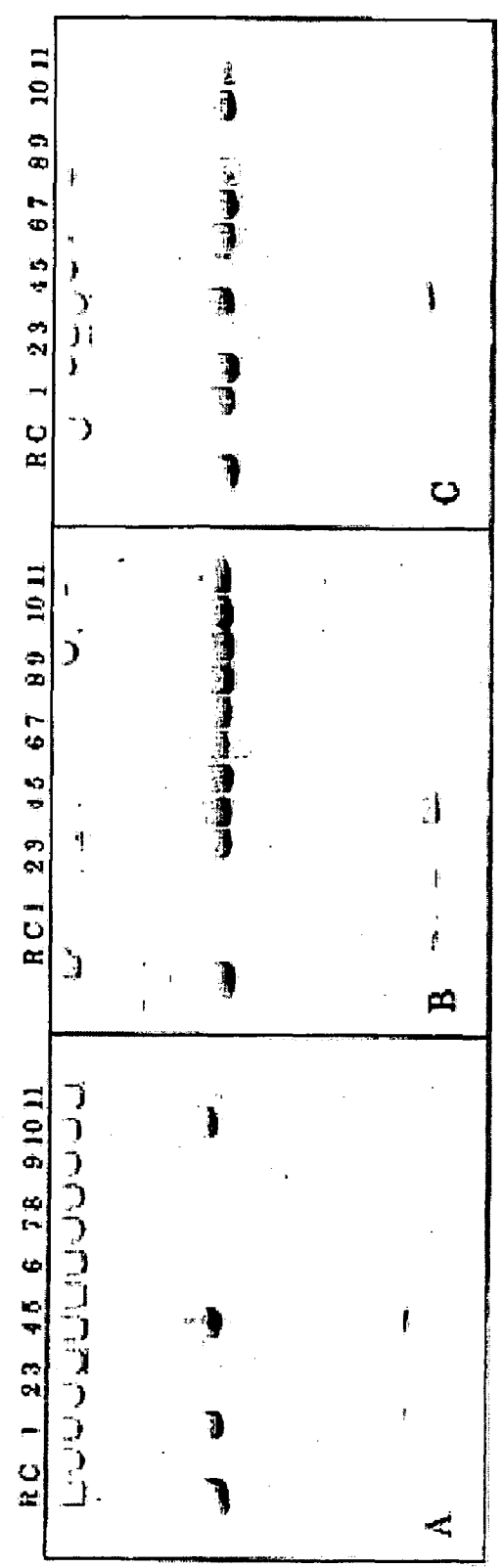
FIG. 2 shows the inhibitory effect of various natural ingredients on the degradation of ovalbumin by active oxygen. A represents oxidative degradation by 10 mM of the ClO radical, B represents oxidative degradation by 10 mM of the OH radical and C represents oxidative degradation by the ONOO radical. The symbols used in each panel are as follows: R is untreated ovalbumin, C is oxidatively degraded control ovalbumin, 1 is chicken extract, 2 is lemon juice, 3 is rice bran extract, 4 is salmon extract, 5 is carrot extract, 6 is mulberry leaf extract, 7 is onion extract, 8 is tea leaf extract, 9 is tumeric extract, 10 is cabbage extract, and 11 is wheat grass extract (the concentrations are shown in Table 2)
Figure 3:
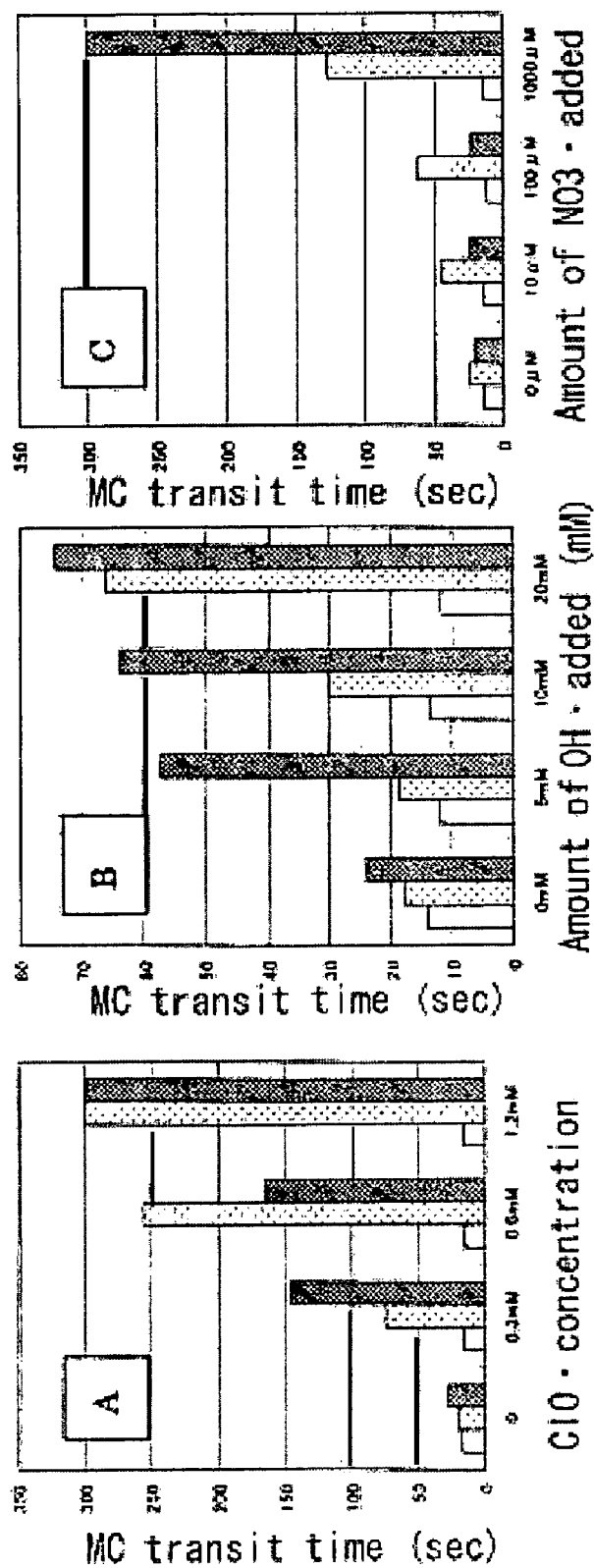
FIG. 3 shows the microchannel transit capability of human blood constituents. A is blood treated with ClO radical, B is blood treated with OH radical and C is blood treated with ONOO radical. The bars in the graph from left to right represent plasma, white blood cells, and red blood cells.
Figure 4:
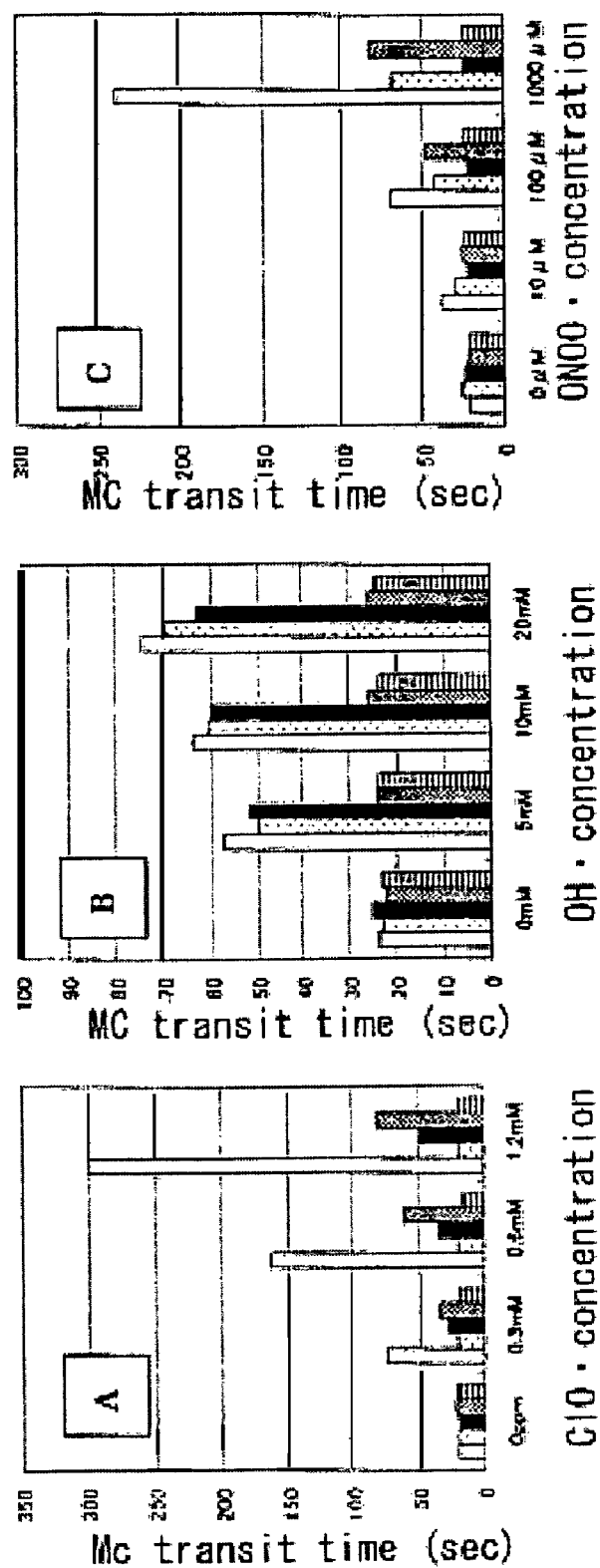
FIG. 4 shows the effect of each active oxygen species on human red blood cells and the effect of each species of antioxidant on microchannel transit capability. A is blood treated with ClO radical, B is blood treated with OH radical, and C is blood treated with ONOO radical. The bars in the graph from left to right represent control, addition of ClO•-scavenger, addition of OH•-scavenger, addition of ONOO•-scavenger, and the mixture of three species of antioxidants.
Figure 5:
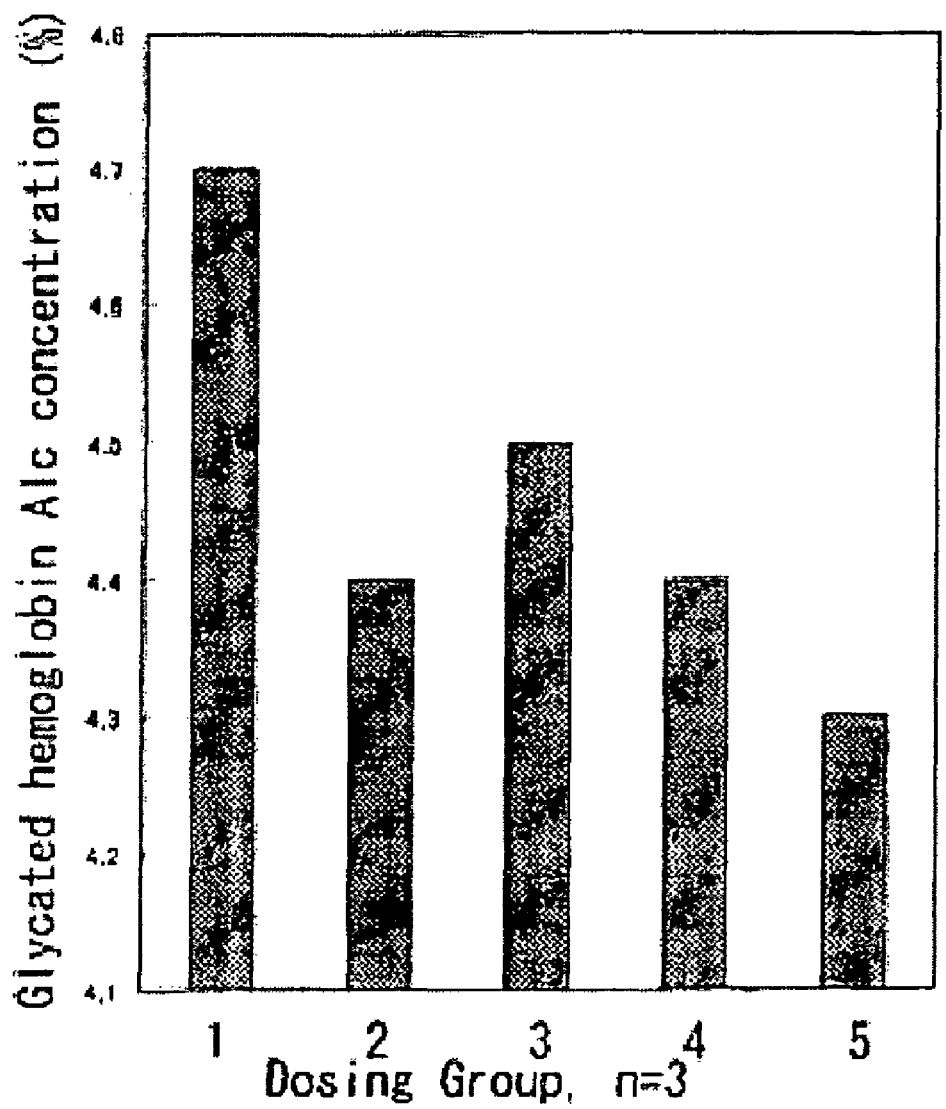
FIG. 5 shows the effect of various species of antioxidants in decreasing the blood HbAlc concentration in diabetes model GK rats.
Figure 6:
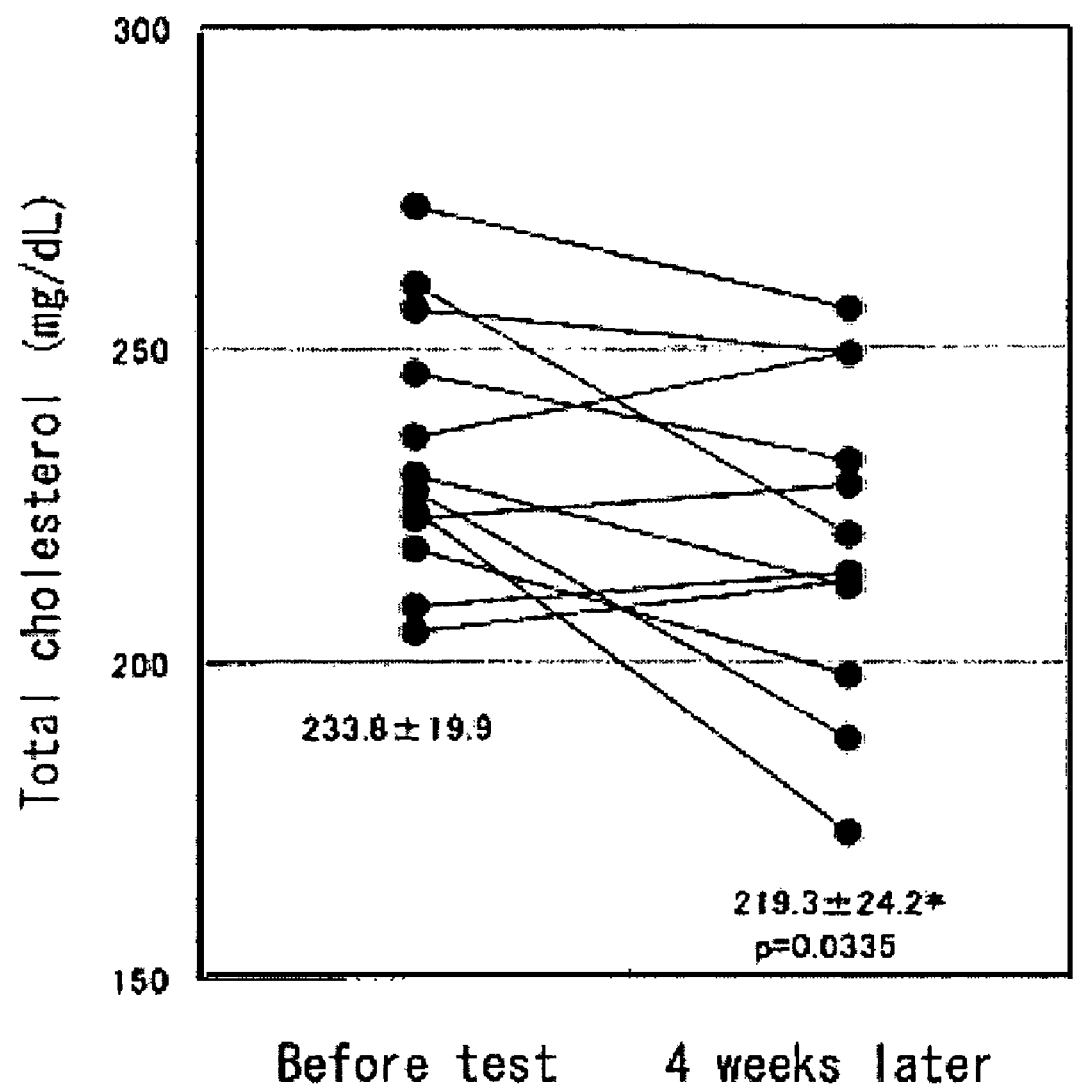
FIG. 6 shows concentration of the total cholesterol in each blood samples of 12 members of healthy volunteers.
Figure 7:
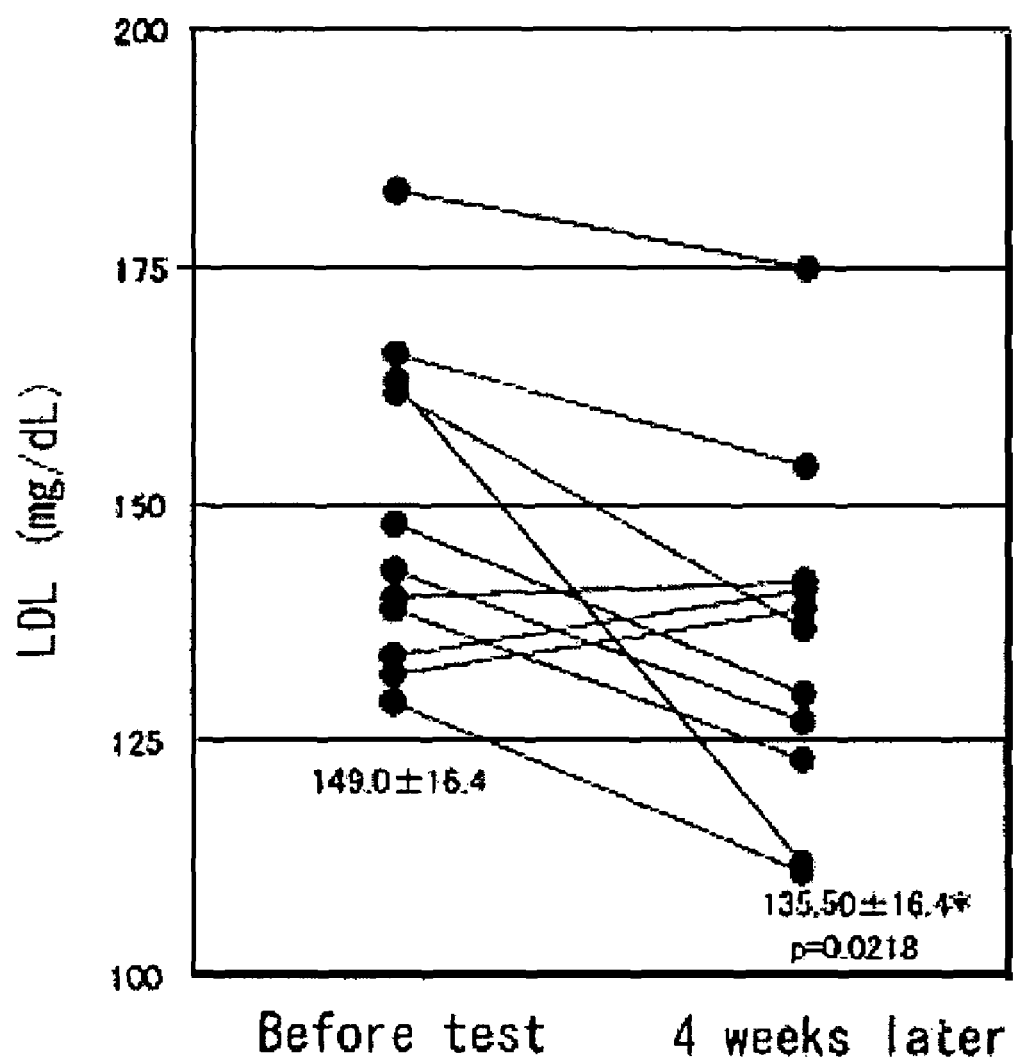
FIG. 7 shows concentration of LDL cholesterol in each blood samples of 12 members of healthy volunteers.
Figure 8:
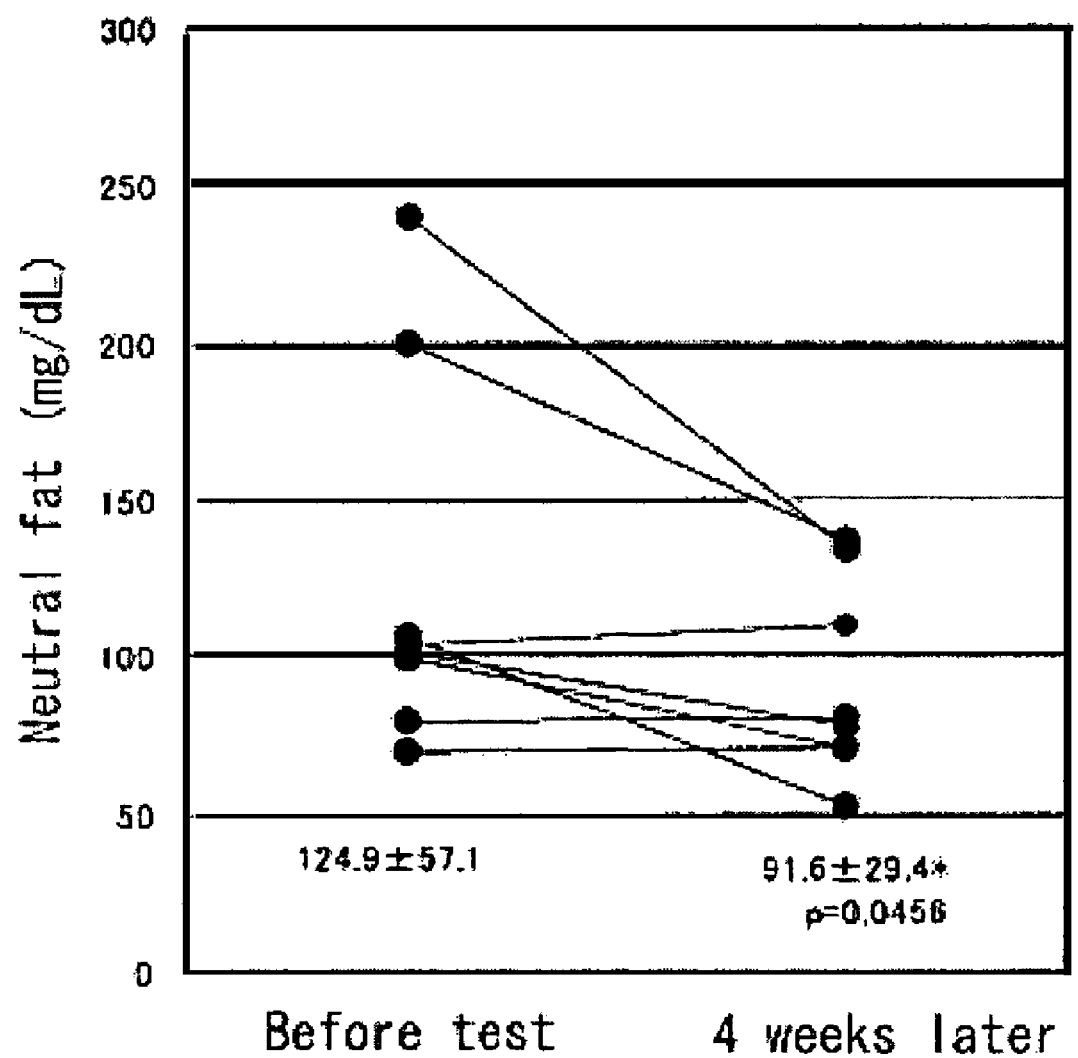
FIG. 8 shows concentration of the neutral fat in blood samples of 8 members with high cholesterol value.
Figure 9:
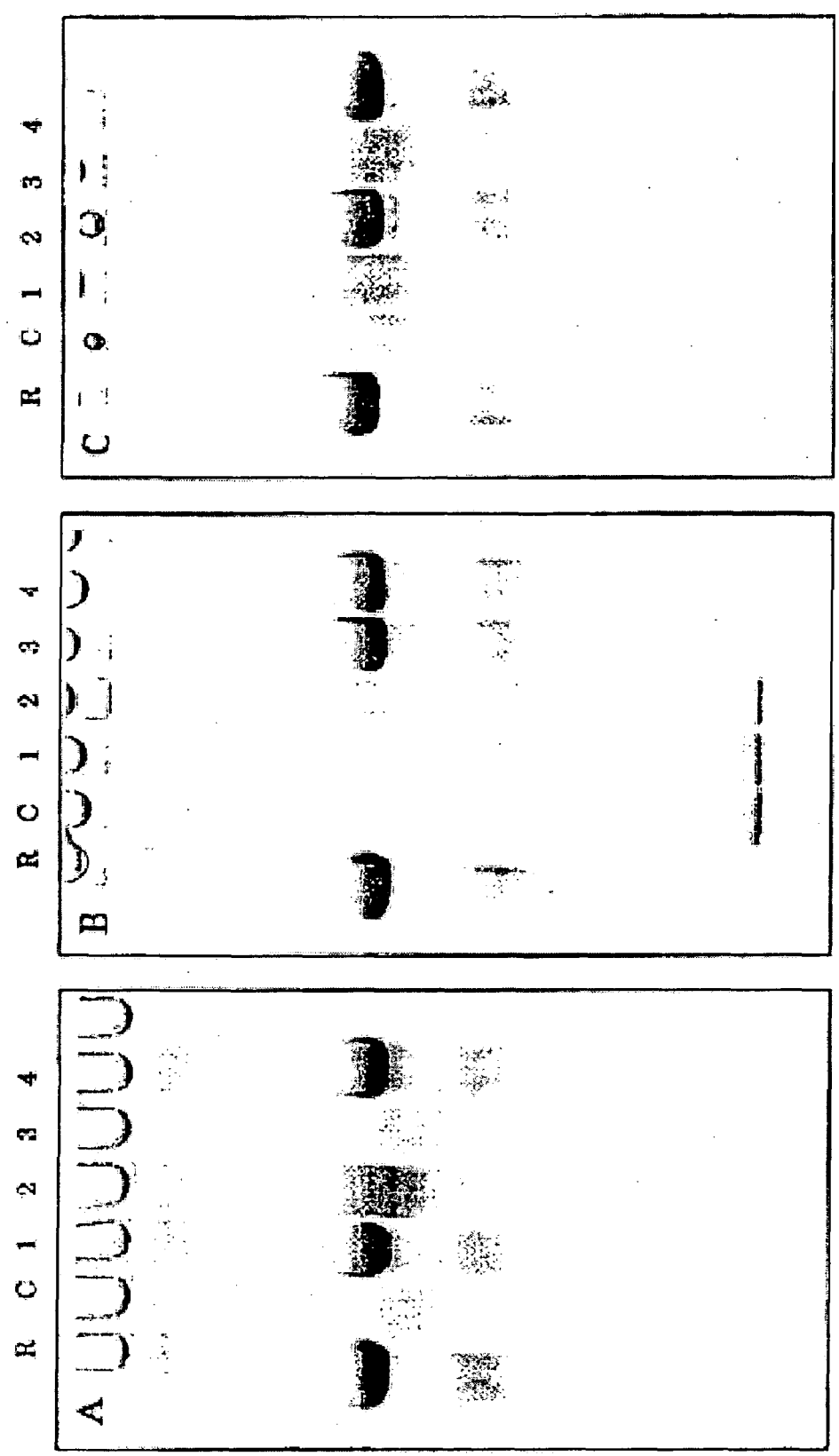
FIG. 9 shows the inhibition effect on the degradation of ovoalbumin due to active oxygen species by each antioxidant. A is the oxidative degradation by 10 mM of ClO radical, B is that by 10 mM of OH radical and C is that by ONOO radical. In each panel, R is untreated ovoalbumin, C is oxidatively degradated ovoalbumin as blank, 1 is 5 mM of anserine-carnosine mixture from chicken extract, 2 is 5 mM of vitamin C, 3 is 50 µM of CoQ10, and 4 is antioxidant arranged with the above three ingredients.
Figure 10:
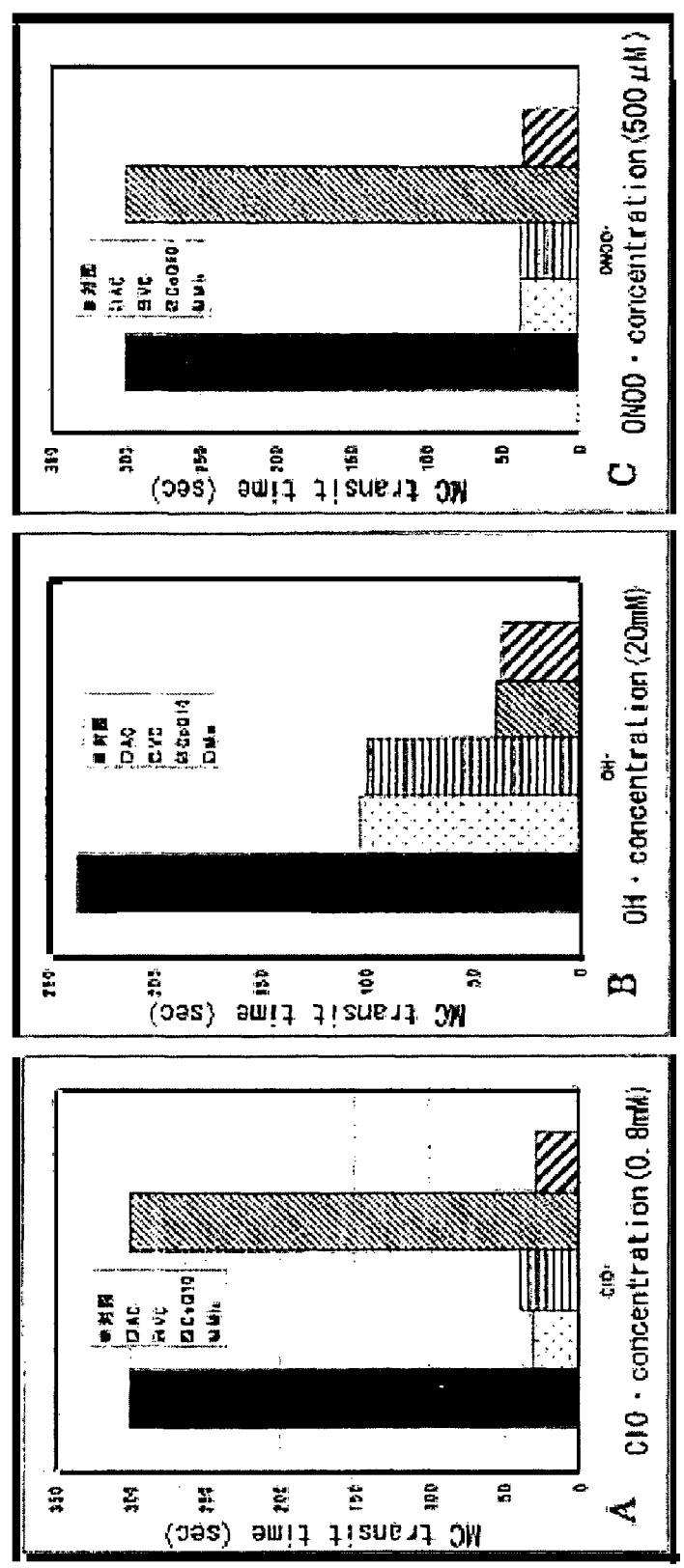
FIG. 10 shows effectiveness of antioxidants in preventing damage by active oxygen on the microchannel transit capability of human red blood cells. Panel A is the oxidative degradation by 10 mM of ClO radical, panel B is that by 10 mM of Oh radical, panel C is that by 5 mM of ONOO radical. Each panel shows, from left to right, a blank without any antioxidants, added with anserine-carnosine from chicken extract, added with vitamin C, added with CoQ10, and added with these 3 ingredients respectively.
Figure 11:
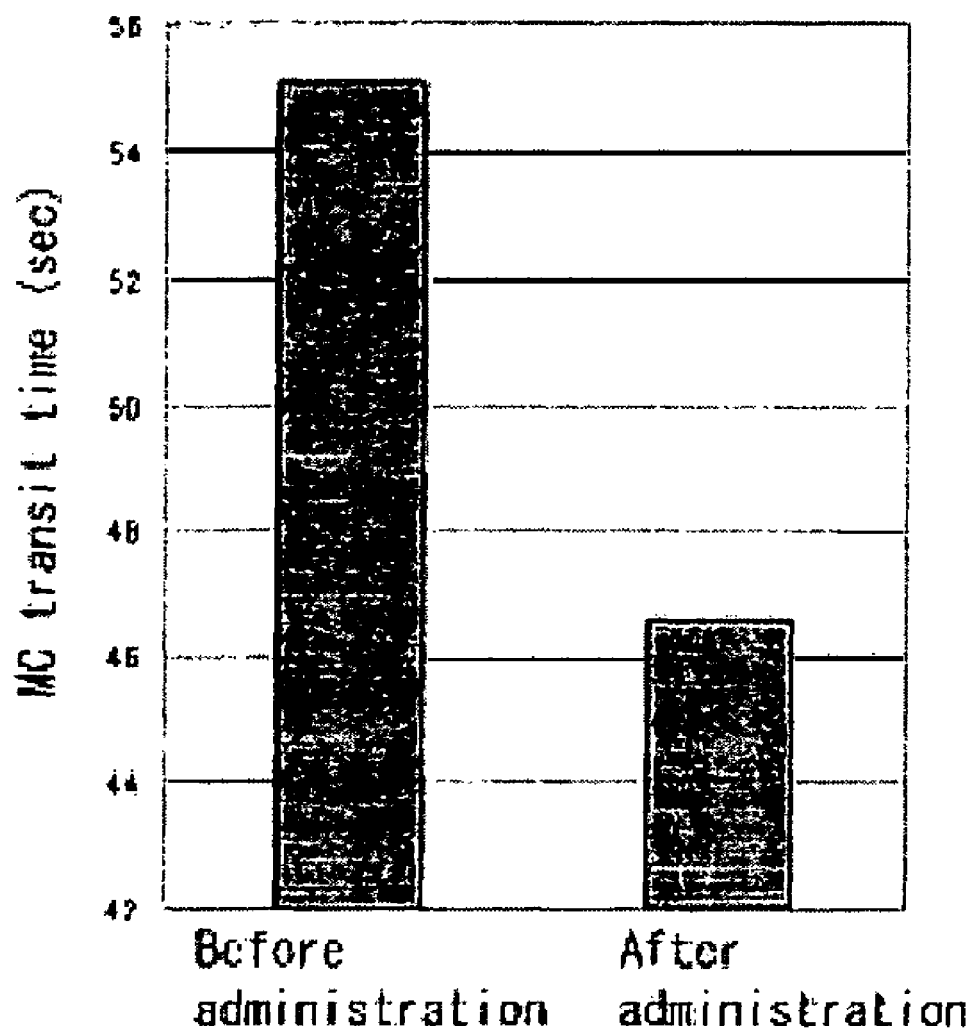
FIG. 11 shows effect on the improvement of the liquidity of blood of healthy volunteers.

Next, the present invention will be specifically described based on examples, but the present invention is not intended to be limited to the examples below.

Example 1

A 20% solid concentrate was prepared by vacuum concentration of 40 L of chicken extract obtained by hot water extraction from 10 kg of whole chicken carcasses. The content of anserine-carnosine mixture in this concentrated chicken extract was 140 mg/g per solid substance. To 1200 g of the concentrated chicken extract were added 16.8 g of V.C. (food additive) and 840 g of concentrated wheat grass extract prepared by obtaining an extract by hot water extraction from wheat grass and concentrating it to contain 10% solids and a 0.2% caffeic acid analogues; 60 g of non-digestible dextrin was added and mixed; and spray drying was performed to obtain approximately 400 g of antioxidant composition powder containing an ClO•-scavenger, OH•-scavenger, and ONOO•-scavenger. The final content was 84 mg of anserine-carnosine, 42 mg of V.C., and 4 mg of caffeic acid analogues per 1 g of powder. It was confirmed that this powder exhibits a blood HbAlc level lowering effect in tests using the aforementioned diabetes model rats.

Example 2

To 5 kg of gutted and boned salmon was added 15 kg of water, and the mixture was boiled for 3 hr at 100° C., and then homogenized in a mixer; a 0.2% concentration of proteolytic enzyme was added, and hydrolysis was performed for 4 hr at 45° C. to prepare a red salmon paste. To 20 kg of the red salmon paste was added 1 kg of the concentrated whole chicken extract from Example 1, 60 g of sodium V.C., 10 g of green tea extract powder (catechin content 20%), 40 g of seasoning liquid, and 100 g of dextrin; and spray drying was performed to prepare approximately 2 kg of salmon extract containing the antioxidant mixture. The content was 50 mg of anserine-carnosine, 25 mg of V.C., 1 mg of astaxanthin as total carotenoid, and 10 mg of catechins per 1 g of powder. A 1% solution of this powder completely inhibited the proteolytic action of the three active oxygen species.

Example 3

To 10 kg of pork was added 30 kg of water and the mixture was heated for 2 hr at 100° C. to obtain a liquid extract; the extract was filtered to remove precipitates and vacuum concentrated to prepare approximately 4 g of concentrated pork extract containing 10% solids. To this was added 1 kg of onion extract (solid content 10%), 100 g of sodium V.C., and 100 g of wheat grass extract powder (caffeic acid analogue content 1.5%); spray drying was then performed to prepare approximately 600 g of pork extract powder for stew containing the antioxidant mixture. The content was 85 mg of anserine-carnosine mixture, 140 mg V.C., and 1 mg of quercetin and 2 mg of the caffeic acid analogue ferulic acid as polyphenols per 1 g of powder. A 1% aqueous solution of this powder completely inhibited the proteolytic action of the three active oxygen species.

Example 4

Chicken extract was filtered through a 3,000 molecular weight fraction ultrafiltration membrane (SEP-3013, Asahi Kasei Corporation), and the filtrate that passed through the ultrafiltration membrane was concentrated to purify the anserine-carnosine mixture using a chromatograph packed with Dowex 50Wx8 cationic exchange resin. Separately, rice bran extract obtained from the hot water extraction of rice bran was added to activated carbon, and decolorization, filtering, and concentration to a solid content of 20% were performed to prepare a concentrated rice bran extract containing caffeic acid analogues. In addition, grapefruit were placed in a mixer and after mixing, the fruit juice obtained thereby was filtered to remove insolubles. To 100 mL of grapefruit juice was added 500 mg of the aforementioned purified anserine-carnosine mixture, 10 mL of rice bran extract (ferulic acid content 30 mg), 200 mg of V.C., 1 g of sweetener, and a suitable amount of natural grapefruit flavoring to prepare a soft drink containing an antioxidant mixture. A 10-fold aqueous dilution of the fruit drink completely inhibited the proteolytic action of the three active oxygen species.

Example 5

To 50 mL of mango juice was added, 400 mg of the purified anserine-carnosine mixture prepared by the method of the example 4, 20 mg of the purified ferulic acid extracted from rice bran (made by Chikuno Rice Fine Chemicals) and 300 mg of the vitamin C (food additive) to prepare 3000 pieces of antioxidant food drinks.

Example 6

To 50 mL of the mango juice (60%), 400 mg of anserine-carnosine mixture from chicken extract, 300 mg of V.C. (food additive) and 0.2 g (20 mg as CoQ10) of water soluble CoQ10 emulsion (made by Yokohama oils and fats) were added to procude juice drink containing the above three antioxidative ingredients. It was observed that this juice drink, as shown in the above text example (7), had the effect of improving the liquidity of the blood samples of the healthy volunteers.

Example 7

The chicken extract obtained by boiling-water extraction of hole chicken was concentrated, freeze-dried to produce chicken extract powder containing 10% of anserine-carnosine. To 2.0 g of the chicken extract powder, 150 mg of V.C. (food additive), 200 mg (10 mg as CoQ10) of CoQ10 (made by Nisshin pharma), further, 80 g of corn powder, 1 g of onion powder and 1 g of seasoning were added to produce instant corn soup powder. This corn soup powder 12.6 g was dissolved into 100 mL of 80° C. hot water to obtain corn potage soup enriched with the antioxidant composition.

By the results of the test, it was revealed that this soup showed the effect of inhibiting the oxidative degradation of the protein by the three active oxygen species produced in the body.

As described in detail above, the present invention relates to an antioxidant composition, and antioxidant compositions that act effectively against a wide range of active oxygen species can be provided thereby. In the past foods containing a single antioxidant have been widely used to prevent aging and prevent lifestyle related diseases. For example, there are various diseases wherein arteriosclerosis and hypertension, cancer, diabetes and various diseases accompanied with diabetes. However, in clinical studies of antioxidants on the prevention of lifestyle diseases and aging that have been conducted in the past, satisfactory results have not always been obtained. There are many possible causes, but first, the clinical effectiveness obtained in vitro and by forced administration to animals may not be realized in humans due to problems with gastrointestinal absorption and distribution throughout the body when taken orally. Second, the active oxygen in the body that causes aging and lifestyle diseases is not a single entity and various species are produced depending on the physiological conditions and lifestyles of human beings. In the past the strength of antioxidant activity has been evaluated using active oxygen that has only meager correlation with the active oxygen produced in the body, and the ranking of intensity has been stipulated using those criteria. However, as verified in the tests of the present invention, the actions of various species of antioxidant at physiologically relevant concentrations are specific with respect to each active oxygen species, and it has become clear that substances that have been evaluated in the past as having weak antioxidant activity demonstrate powerful antioxidant activity against a specific active oxygen species, and conversely, substances that have been evaluated as having strong antioxidant activity actually have only weak activity against some active oxygen species. Based on these findings, with foods having a single antioxidant as the main ingredient it has been impossible to satisfactorily prevent various diseases that emerge due to various active oxygen species produced in the body.

In the present invention the active oxygen species produced in the body are divided into three groups, and antioxidants for the active oxygen species of the OH• system produced from oxygen gas, and of the chlorine system and nitric oxide system produced by white blood cells are identified. As a result, the present invention has revealed that peptides and sulfur-containing amino acids that constitute peptides have a strong antioxidant action against the active oxygen of the chlorine system, carotenoids and polyphenols from plans and substances that have a hydrophobic group such as phenols have a strong antioxidant action against the active oxygen of the OH• system, and vitamin C, etc., have a strong antioxidant action against the active oxygen of the nitric oxide system. From these findings it is important that an antioxidant composition act effectively against a wide range of active oxygen species, and in fact, because it has been recognized that the combined use of antioxidants markedly inhibits the production of ultimately glycated products in the body that occur due to oxidative damage, it is possible to provide antioxidant foods that are even more effective in preventing the emergence of aging and lifestyle disease than in the past. In addition, it is possible to manufacture antioxidant food ingredients that are even more effective by combining natural ingredients that contain these antioxidant constituents.

What is claimed is:

1. A composition that does not contain vitamin E, comprising in the following proportions:
   (A) 100 mg anserine and carnosine,
   (B) 20 mg to 164.7 mg of Vitamin C, which may be in the form of L-ascorbic acid or L-ascorbate, and
   (C) 2 mg to 5 mg of at least one caffeic acid compound selected from the group consisting of ferulic acid, curcumin, chlorogenic acid, cinnamic acid, and caffeic acid.

2. The composition of claim 1, wherein (C) is caffeic acid.

3. The composition of claim 1, wherein (C) is ferulic acid.

4. The composition of claim 1, wherein (C) is chlorogenic acid.

5. The composition of claim 1, wherein (C) is curcumin.

6. The composition of claim 1, wherein (C) is cinnamic acid.

7. The composition of claim 1 in an ingestible and intestinally absorbable form.

8. A food to which the composition of claim 1 has been added.

\* \* \* \* \*